United States Patent [19]

Beaty et al.

[11] Patent Number: 5,364,953
[45] Date of Patent: Nov. 15, 1994

[54] HIGH RELAXIVITY, PARAMAGNETIC, METAL CLUSTERS FOR MAGNETIC RESONANCE IMAGING

[75] Inventors: Julie A. Beaty, Florissant; Edward A. Deutsch, Maryland Heights; Dennis L. Nosco, Florissant, all of Mo.

[73] Assignee: Mallinckrodt Medical, Inc., St. Louis, Mo.

[21] Appl. No.: 971,789

[22] Filed: Nov. 5, 1992

[51] Int. Cl.$^5$ ................ A61K 49/00; C07F 11/00; C07F 13/00; C07F 15/00
[52] U.S. Cl. ................ 556/46; 556/58; 556/112; 556/140; 424/9; 534/15
[58] Field of Search ............ 424/9; 546/88, 2, 6, 546/8, 10; 534/15; 556/46, 58, 112, 140

[56] References Cited

U.S. PATENT DOCUMENTS

| | | | |
|---|---|---|---|
| 4,832,877 | 5/1989 | Bino et al. | 260/414 |
| 4,935,518 | 6/1990 | Rocklage et al. | 546/6 |

FOREIGN PATENT DOCUMENTS

| | | | |
|---|---|---|---|
| WO90/03190 | 4/1990 | WIPO | A61K 49/00 |
| WO91/14460 | 10/1991 | WIPO | A61K 49/04 |
| WO92/17215 | 10/1992 | WIPO | A61K 49/04 |

OTHER PUBLICATIONS

Nadine De Vries et al., "Reduction of $Mn_{12}O_{12}$-$(O_2CPh)_{16}(H_2O)_4$ to Give High Spin Materials with Various Counterions", Abstracts of 203rd meeting of the American Chemical Society, San Francisco, Calif., Apr. 5–10, 1992.
Ansell et al; J. Chem. Soc., Chem. Commun. 063. 1982. pp. 546–547.
Cotton et al., "Further Studies of $M_3(\mu_3-O)(\mu-X)_3$-$(\mu-O_2CCH_3)_3L_3$(M = Mo,W) Type Clusters with Nine Core Electrons," *Journal of Cluster Science*, vol. 3, No. 2, pp. 123–144, 1992.
Shibahara et al., "Syntheses and Electrochemistry of Incomplete Cubane-Type Clusters with $M_3S_4$ Cores (M = Mo, W). X-ray Structures of $[W_3S_4(H_2O)_9](CH_3C_6H_4SO_3)_4.9H_2O$, $Na_2[W_3S_4(Hnta)_3].5H_2O$, and $(bpyH)_5[W_3S_4(NCS)_9].3H_2O$," *Inorg. Chem.*, vol. 31, No. 4, pp. 640–647, 1992.
Chisholm et al., "Synthesis and Crystal and Molecular Structure of $Mo_4O(OCH_2Bu^t)_{10}(py)$: A 12-Electron Butterfly Cluster," *Journal of Cluster Science*, vol. 3, No. 2, pp. 151–165, 1992.
Caneschi et al., "Alternating Current Susceptibility, High Field Magnetization, and Millimeter Band EPR Evidence for a Ground S=10 State in $[Mn_{12}O_{12}(CH_3COO)_{16}(H_2O)_4].2CH_3COOH.4H_2O$," *J. Am. Chem. Soc.*, vol. 113, pp. 5873–5874, 1991.
Cotton et al., "Preparations, Structures, and Properties of $M_3X_{13}$ Type Molybdenum and Tungsten Trimers with Eight Cluster Electrons," *J. Am. Chem. Soc.*, vol. 113, No. 8, pp. 3007–3011, 1991.
Mussell et al., "Partitioning of the Electrochemical Excitation Energy in the Electrogenerated Chemiluminescence of Hexanuclear Molybdenum and Tungsten Clusters," *Inorg. Chem.*, vol. 29, No. 19, pp. 3711–3717, 1990.
Gomez-Garcia et al., "Mixed-valence trinuclear manganese clusters: Influence of the electronic transfer on the magnetic properties," *J. Appl. Phys.*, vol. 67, No. 9, pp. 5992–5994, 1990.
Chisholm et al., "Twelve-Electron Tetranuclear Tungsten Alkoxide Clusters are not Tetrahedral. Preparation, Structure and Bonding in $W_4(O)$ $(OPr^i)_{10}$ and $W_4(O)(CI)$ $9OPr^i)_9$. Comparisons with the Bonding in Carbonyl Clusters," *Polyhedron*, vol. 9, No. 15 16, pp. 1829–1841, 1990.
Chisholm et al., "Hexaisopropoxyditungsten and
(List continued on next page.)

Primary Examiner—Marianne M. Cintins
Assistant Examiner—Phyllis G. Spivack
Attorney, Agent, or Firm—Brian K. Stierwalt

[57] ABSTRACT

The present invention relates to novel compounds for use as imaging agents. In particular, the present invention relates to paramagnetic metal clusters having oxygen and/or nitrogen containing ligands useful as contrast agents for magnetic resonance imaging (MRI).

7 Claims, No Drawings

OTHER PUBLICATIONS

Dodecaisopropoxytetratungsten: $W_2(O\text{-}i\text{-}Pr)_6$ and $W_4(O\text{-}i\text{-}Pr)_{12}$. 2. Studies of Cluster Dynamics and the Equilibrium between the 12-Electron Cluster and Two Metal-Metal Triple Bonds. A Symmetry-Allowed $[\pi^2_s+\pi^2_s]$ Cycloaddition Reaction and Comparisons with the Chemistry of Cyclobutadiene[2]," *J. Am. Chem Soc.*, vol. 111, No. 2, pp. 574–586, 1989.

Boyd et al., "Potential Building Blocks for Molecular Ferromagnets: $[Mn_{12})_{12}(O_2CPh)_{16}(H_2O)_4]$ with a $S=14$ Ground State", *J. Am. Chem. Soc.*, vol. 110, No. 25, pp. 8537–8539, 1988.

Bino et al., "Further Studies of the Monooxo-Capped Tritungsten Carboxylate Clusters," *Inorg. Chem.*, vol. 27, No. 20, pp. 3592–3596, 1988.

Chisholm et al., "Tetranuclear Halide-Alkoxide Clusters of Molybdenum Formed by the Coupling of M-M Triple-Bonded Dinuclear Compounds. Synthesis, Characterization, and Molecular Structures of $Mo_4F_2(O\text{-}i\text{-}Pr)_{10}$ $Mo_4X_3(O\text{-}i\text{-}Pr)_9$ and $Mo_4X_4(O\text{-}i\text{-}Pr)_8$ (X=Cl, Br, I)," *Inorg. Chem.*, vol. 27, No. 12, pp. 2071–2097, 1988.

Vincent et al., "Preparation and Physical Properties of Trinuclear Oxo-Centered Manganese Complexes of the General Formulation $[Mn_3O(O_2CR)_6L_3]^{0,+}$ (R=Me or Ph; #L=a Neutral Donor Group) and the Crystal Structures of $[Mn_3O(O_2CMe)_6(pyr)_3](pyr)$ and $[Mn_3O(O_2CPh)_6(pry)_2(H_2O)]\cdot 0.5$ MeCN," *J. Am. Chem. Soc.*, vol 109, No. 19, pp. 5703–5711, 1987.

Chisholm et al., "Hexaisopropoxyditungsten and Dodecaisopropoxytetratungsten: $W_2(O\text{-}i\text{-}Pr)_6$ and $W_4(O\text{-}i\text{-}Pr)_{12}$. 1. Preparation, Structure, and Bonding. The First Example of a Metal-Metal Triple Bond and Its 12-Electron Cluster Analogies with Ethyne and Cyclobutadiene," *J. Am. Chem Soc.*, vol. 109, No. 25, pp. 7750–7761, 1987.

F. Albert Cotton, "Highlights of Recent Research on Compounds with Mo-Mo Bonds," *Polyhedron*, vol 5, No. 12, pp. 5–14, 1986.

"E. Molybdenum-Sulfur Clusters," pp. 254–275, 1986.

Cotton et al., "The First Alkylidyne-Capped Tritungsten(IV) Cluster Compounds: Preparation, Structure, and Properties of $[W_3O(CCH_3)(O_2CCH_3)_6(H_2O)_3]Br_2\cdot 2H_2O$," *Inorg. Chem.*, vol. 24, No. 25, pp. 4381–4384, 1985.

Chisholm et al., "Metal Alkoxides: Models for Metal Oxides. 7. Trinuclear and Tetranuclear Alkylidyne Clusters of Tungsten Supported by Alkoxide Ligands," *J. Am. Chem. Soc.*, vol. 107, No. 5, pp. 1234–1241, 1985.

Cotton et al., "Synthesis and Structure of New Trinuclear Cluster Compounds $[M_3(\mu_3-O)_2(O_2CC_3H_7)_6(H_2O)_3]^{2+}$ (M=Mo, W). Comparison of Mo and W Bond Radii as a Function of M—M Bond Order," *Inorg. Chem.*, vol. 23, No. 26, pp. 4738–4742, 1984.

Cotton et al., "New Preparative Methods, Structure, and Nitration of Bi-oxo-capped Trimolybdenum(IV) and Tritungsten(IV) Cluster Cations," *Inorg. Chem.*, vol. 23, No. 24, pp. 4033–4038, 1984.

Cotton et al., "A Trinuclear Tungsten(IV) Cluster Compound with a Capping Chlorine Atom and Three Bridging Oxygen Atoms," *Inorg. Chem.*, vol. 20, No. 7, pp. 2219–2223, 1981.

Muller et al., "Trinuclear Clusters of the Early Transition Elements," *Angew. Chem. Int. Ed. Engl.*, vol. 19, pp. 875–882, 1980.

Bino et al., "A New Class of Trinuclear Tungsten(IV) Cluster Compounds with W—W Single Bonds," *Inorg. Chem.*, vol. 17, No. 11, pp. 3245–3253, 1978.

Hogue et al., "Chemistry of Polynuclear Metal Halides. V. Reactions and Characterization of Compounds Containing Tungsten Halide Cluster Species," *Inorg. Chem.*, vol. 19, pp. 1354–1359, 1970.

HIGH RELAXIVITY, PARAMAGNETIC, METAL CLUSTERS FOR MAGNETIC RESONANCE IMAGING

BACKGROUND

The present invention relates to novel compounds for use as imaging agents. In particular, the present invention relates to paramagnetic metal clusters with oxygen and/or nitrogen containing ligands useful as contrast agents for magnetic resonance imaging (MRI), magnetic resonance spectroscopy (MRS), and magnetic resonance spectroscopy imaging (MRSI).

The phenomenon of NMR was discovered in 1945, but only recently has found application for enhancing images of internal body structures, such as organs and tissues. The technique of MRI involves the detection of certain atomic nuclei; i.e. those possessing magnetic dipole moments, utilizing magnetic fields and radio-frequency radiation.

The images produced by MRI provide a cross-sectional display of body anatomy and give excellent resolution of soft tissue detail. The images are usually produced by mapping a distribution of protons and their relaxation times in the organs or tissues. Because there is a lack of any known hazard associated with the level of the magnetic and radio-frequency fields that are employed using MRI techniques, repeated scans of individuals can be performed without risk. MRI techniques are also advantageous as they are non-invasive, avoiding the use of ionizing radiation. Additionally, MRI techniques allow for any scan plane to be readily selected, including transverse, coronal, and sagittal sections.

It is believed that MRI has a greater potential for selective examination of tissue characteristics than other known techniques, such as X-ray computed tomography (CT). This is because the known techniques rely on a limited number of coefficients to determine image contrast, such as X-ray attenuation and coefficients for CT, while the MRI signal relies on at least four variable; T1, T2, proton density, and flow. Also, MRI is more sensitive to subtle physicochemical differences between organs and tissues, and it is therefore believed that MRI may be capable of differentiating different tissue types and detecting diseases which induce physicochemical changes that may not be detected by other known techniques, such as CT which is only sensitive to differences in the electron density of tissue.

The hydrogen atom, which has a nucleus consisting of a single unpaired proton, has the strongest magnetic dipole moment of any nucleus. Hydrogen is abundant in the human body, occurring in both water and lipids. Therefore, MRI techniques are most commonly used to produce images based upon the distribution density of hydrogen atoms and the relaxation times of the hydrogen atoms in organs and tissues. However, there are other nuclei which also exhibit a nuclear magnetic resonance phenomenon, such as carbon-13 (six protons, seven neutrons), fluorine-19 (nine protons and ten neutrons), sodium-23 (eleven protons and twelve neutrons), and phosphorus-31 (fifteen protons and sixteen neutrons).

MRI techniques are carried out by irradiation of the desired body area with pulsed radio-frequency (RF) energy in a controlled gradient magnetic field. The nuclei or protons within the applied magnetic field tend to align in the direction of the magnetic field. However, when irradiated with the RF energy pulse, the nuclei or protons are "excited" and their spin is altered. This causes an effective tipping of the nuclei or protons out of the magnetic field direction; the extent of tipping is dependent on the pulse duration and energy. Following the application of the RF pulse, the nuclei or protons "relax" or return to equilibrium and realign with the magnetic field, emitting radiation at the resonant frequency of the nuclei or proton in the process.

The decay of the emitted radiation is characterized by two relaxation times, T1 and T2. T1 is the spin-lattice relaxation time or longitudinal relaxation time, i.e., the time taken by the nuclei or protons to return to equilibrium along the direction of the applied magnetic field. T2 is the spin-spin relaxation time associated with the dephasing of the initially coherent precession of individual proton spins. Relaxation times have been established for various fluids, organs and tissues in different species of mammals.

The relaxation times, T1 and T2 are essentially mechanisms whereby the energy imparted by the RF pulse is subsequently dissipated to the surrounding environment. Therefore, these relaxation times are influenced by the environment of the nuclei, such as viscosity, temperature and the like. In addition, the rate of relaxation may be influenced by other molecules or nuclei which are paramagnetic. Therefore, chemical compounds incorporating paramagnetic molecules or nuclei may substantially alter the T1 and T2 values of nearby nuclei having a magnetic dipole moment. The extent of the paramagnetic effect of the given chemical compound is a function of the environment within which it exists. The ability of MRI to detect these paramagnetic influences is one reason for the higher potential of MRI as compared to other techniques, such as CT, as noted above.

An important aspect of MRI is that as the initial spin number of the contrast agent is increased, the T1 and T2 values may be increased, resulting in superior image quality. Therefore, it is desirable to maximize the spin number of the contrast agent while maintaining other necessary qualities thereof, such as overall neutrality of the agent.

In light of the above, MRI agents having a high spin number, which lead to sharp, clear images, would represent a significant advance in the art.

OBJECTS OF THE INVENTION

It is one object of the present invention to provide novel MRI contrast agents having superior imaging qualities.

It is another object of the present invention to provide novel MRI contrast agents having initially high in vitro relaxivity.

SUMMARY OF THE INVENTION

The above objects and others are accomplished according to the present invention by providing contrast agents based on high relaxivity, paramagnetic, metal clusters. In particular, the present invention relates to contrast agents involving metal clusters with or without oxo groups, substituted with oxygen and/or nitrogen containing ligands. Further, the present invention relates to contrast agents as described above, having additional substitution of neutral ligands or ligands with pendent cationic groups which can alter the overall charge of the metal cluster to give neutral or low charged anionic or cationic MRI contrast agents.

DETAILED DESCRIPTION OF THE INVENTION

Metal clusters having oxygen and/or nitrogen containing ligands have common features which indicate that these clusters could be useful as potential MRI contrast agents. In particular, all of the structures are composed of multiple metal atoms and are held together by metal—metal and/or bridging ligand bonding. A particular advantage of clusters with paramagnetic metals is the possibility of having large numbers of unpaired electrons per molecule, and thus, very high relaxivities.

The present invention relates to MRI contrast agents made up of substituted paramagnetic metal clusters having oxygen and/or nitrogen containing ligands, and having high spin numbers, and low or neutral overall charge.

Examples of paramagnetic metals which can be included in the clusters are Cr, Mn, Fe, Co, Ni, Cu, Pr, Nd, Sm, Y, Gd, Tb, Dy, Ho and Er. Preferably, the paramagnetic metals are transition metals having low valent states. Further, the paramagnetic metal clusters of interest for use in MRI contrast agents preferably have from 2 to 12 metal atoms.

The oxygen and/or nitrogen containing ligands may be any mono- or multidentate ligand capable of binding to the paramagnetic metal in a bridging or terminal manner. Examples of oxygen containing ligands include mono- or poly-, alkoxy, carboxylate, sulfonate, boronate, and phosphonate ligands.

The present invention particularly relates to MRI contrast agents having the following general formula:

$$M_A O_B L_D Q_Z Y_X$$

wherein
M is a paramagnetic metal atom,
A is 2 to 12,
O is an oxygen atom,
B is 0 to 12,
L is a first ligand,
D is 0 to 12,
Q is a substitution group,
Z is 2 to 16,
Y is a second ligand, and
X is 0 to 12.

The paramagnetic metal atom, M, may be any metal atom having a relatively high spin number, such as Cr, Mn, Fe, Co, Ni, Cu, Pr, Nd, Sm, Y, Gd, Tb, Dy, Ho and Er. Preferably the paramagnetic metal atom is Mn or Fe. It is also desirable that the metal be in a low valence state, e.g. +2 for Mn or Fe.

The substitution group, Q, may be any group which provides an oxygen or other donating atom that can bind to the metal. In particular, the substitution group may have the following general formula:

$$(O_a G)_b R$$

wherein
O is an oxygen atom,
a is 1 to 2,
G is any element from group IIIA, IVA, VA, or VIA of the periodic table; preferably, C, P, S, N, B, or Si,
b is 1 to 4, and
R is selected from the group consisting of hydrogen, alkyl, aryl, hydroxyl, alkoxyl, mono- or poly-hydroxyalkyl, mono- or poly-alkoxyalkyl, acyl, alkoxycarbonyl, or carbamoyl.

Preferably, the substitution group, Q, is a mono- or di-, alkoxy, carboxylate, sulfonate, boronate, or phosphonate. Further, the substitution group, Q, may be a dicarboxylic acid having a chain length of 2 to 8 substituted or unsubstituted carbon atoms, wherein such dicarboxylic acid takes the place of two ($O_a G$) groups in the above formula.

The first and second ligands, L and Y, may be any appropriate ligand that binds to the metals and that may provide extra stability and favorable biodistribution characteristics. The ligands, L or Y, may have all of their respective bonding sites attached to a single metal atom within the cluster or may bridge two or more metal atoms. In particular, the ligands may be selected from the group consisting of mono-dentate, bi-dentate, tri-dentate and tetra-dentate ligands.

Ligands which may be present as the ligands L or Y, include ligands such as phenanthroline, pyridine, bipyridine 2,2'-bis-(1-methylimidazole)-phenyl-methoxymethane and pharanthroline or bipyridine derivatives such as 4,4'-diphenyl-2,2'-bipyridine, 2,9-dimethyl-4,7-biphenyl-1,10-phenanthroline, 4,7-diphenyl-1,10-phenanthroline, 5-chloro-1,10-phenanthroline, 5-methyl-1,10-phenanthroline, and 3,4,7,8-tetramethyl-1,10-phenanthroline.

Also, further according to the present invention, the ligands L and Y and the substitution group Q may be combined to form a multidentate ligand.

There are a number of compounds known in the prior art that meet the requirements of the above formulas and descriptions. However, none of these compounds have previously been investigated for their potential as MRI contrast agents. Accordingly, the present invention is directed to the recognition and development of paramagnetic metal clusters with oxygen and/or nitrogen containing ligands.

The following examples provide information relative to the use of various compounds which meet the criteria noted above, as MRI contrast agents.

EXAMPLE 1

[Mn$_3$(OAc)$_6$(phen)$_2$]

A solution containing 1.0828 g (0.00546 mole) of 1,10-phenanthroline.H$_2$O (phen) in 35 mL DMF was added to a stirred solution of Mn$_3$(OAc)$_2$.4H$_2$O (2.0050 g, 0.00818 mole) in 50 mL DMF. A yellow precipitate formed almost immediately upon addition of the phenanthroline. The mixture was allowed to stir for 30 minutes at which time the yellow solid was collected by filtration and dried. (Yield=98%)

FT-IR(KBr): 3057, 2999, 2930, 1587, 1514, 1423, 1342, 1221, 1149, 1140, 1101, 1047, 1015, 942, 864, 849, 776, 657, and 640 cm$^{-1}$.

Anal. Calcd. for C$_{36}$H$_{34}$Mn$_3$N$_4$O$_{12}$: C, 49.16; H, 3.90; N, 6.37; Mn, 18.77. Found: C, 48.34; H, 4.16; N, 6.70; Mn, 17.61.

Relaxivities: R$^1$=20.45 mM$^{-1}$sec$^{-1}$ R$^2$=91.25 mM$^{-1}$sec$^{-1}$

Magnetic susceptibility: $\mu$=5.81 B.M.

Solubility: water (0.020M soln ppts. MnO$_2$ upon standing several hrs). Also sol in MeOH.

EXAMPLE 2

[Mn$_3$(OAc)$_6$(bipy)$_2$]

To a solution of Mn$_3$(OAc)$_2$.4H$_2$O (0.9996 g, 0.00408 mole) in 20 mL DMF was added a solution of 2,2'-bipyridine (bipy) (0.4242 g, 0.00272 mole) in 15 mL DMF. After 10 minutes of stirring, precipitate began to form. The mixture was allowed to stir for 3 hours. The resulting yellow solid was collected by filtration and dried. (Yield=81%)

FT-IR(KBr): 3103, 3064, 2997, 2926, 1597, 1473, 1418, 1337, 1314, 1295, 1245, 1154, 1057, 1017, 937, 770, 737, 674, 649; and 624 cm$^{-1}$.

Anal. Calcd. for C$_{32}$H$_{34}$Mn$_3$N$_4$O$_{12}$: C, 46.23; H, 4.12; N, 6.74; Mn, 19.82. Found: C, 46.17; H, 3.82; N, 7.00; Mn, 20.33.

Relaxivities: R$^1$=21.51 mM$^{-1}$sec$^{-1}$ R$^2$=106.613 mM$^{-1}$sec$^{-1}$

Magnetic susceptibility: $\mu$=5.88 B.M.

Solubility: water (0.020M soln ppts. MnO$_2$ upon standing several hrs). Also sol in MeOH.

EXAMPLE 3

[Mn$_3$(OBz)$_6$(phen)$_2$]

To a stirred solution containing 0.391 g (0.001814 mole) of 1,10-phenanthroline.H$_2$O (phen) in 10 mL DMF was added a solution containing 1.0026 g (0.002717 mole) Mn$_3$(OBz)$_2$.4H$_2$O om 10 mL DMF. After approximately 5 minutes, a yellow precipitate formed. Stirring was continued for an hour. Subsequently, the product was collected by filtration and dried. (Yield =91%)

FT-IR(KBr): 3059, 3025, 2930, 1674, 1618, 1562, 1491, 1289, 1173, 1140, 1100, 1067, 1022, 938, 821, 768, and 673 cm$^{-1}$.

Anal. Calcd.: C, 63.31; H, 3.68; N, 4.48; Mn, 13.19. Found: C, 60.94; H, 3.56; N, 4.68; Mn, 12.56.

Relaxivities: R$^1$=19.93 mM$^{-1}$sec$^1$ R$^2$=83.83 mM$^{-1}$sec$^{-1}$

Magnetic susceptibility: $\mu$=4.98 B.M.

Solubility: water (sparingly) 0.0040M soln eventually ppts. MnO$_2$, but not as quickly as the above acetate analogues.

EXAMPLE 4

[Mn$_3$(OBz)$_6$(bipy)$_2$]

A solution containing 0.2820 g (0.001808 mole) of 2,2'-bipyridine (bipy) in 10 mL DMF was added to a solution containing 1.0037 g (0.002720 mole) of Mn$_3$(OBz)$_2$.4H$_2$O in 20 mL DMF. After about 2 hours of stirring, a yellow precipitate formed. This precipitate was collected by filtration and dried. (Yield=77%)

FT-IR (KBr): 3059, 1675, 1604, 1563, 1540, 1463, 1398, 1310, 1172, 1068, 1020, 852, 762, 719, and 685 cm$^{-1}$.

Anal. Calcd.: C, 61.84; H, 3.82; N, 4.66; Mn, 13.72. Found: C, 59.58; H, 3.67; N, 5.02; Mn, 13.03.

Relaxivities: R$^1$=20.08 mM$^{-1}$sec$^{-1}$ R$^2$=101.72 mM$^{-1}$sec$^{-1}$

Magnetic susceptibility: $\mu$=5.55 B.M.

Solubility: water (sparingly) 0.0040M soln ppts. MnO$_2$, but not as fast as above acetate analogues.

Further examples of compounds which may be useful as MRI contrast agents include the following:

[Mn$_3$O(OAc)$_6$(Py)$_3$]
[Mn$_3$O(OBz)$_6$(Py)$_2$(H$_2$O)]
[Mn$_3$(biphen)$_3$(OBz)$_2$(bipy)$_2$]
[Mn$_3$(DBCat)$_4$(Py)$_4$] (DBCat=3,5-di-t-butylcatechol)
[Mn$_4$O$_2$(OAc)$_6$(bipy)$_2$]
[Mn$_4$O$_2$(OBz)$_7$(bipy)$_2$]
[Mn$_4$O$_2$(O$_2$CR)$_7$(PicH)$_2$]— (R=Me, Et, Ph; PicH=picolinic acid)
[Mn$_4$O$_3$Cl$_4$(O$_2$CR)$_3$(Py)$_3$] (R=Me, Ph)
[M$_4$(DBCat)$_4$(Py)$_6$] (M=Mn, Fe)
[Mn$_4$O$_2$(OAc)$_6$(Py)$_2$(dbm)$_2$] (dbm=dibenzoylmethane)
[Mn$_6$O$_2$(OBz)$_{10}$(Py)$_2$(MeCN)$_2$]
[Mn$_6$O$_2$(OBz)$_{10}$(Py)$_4$].Et$_2$O
[Mn$_9$O$_4$(OBz)$_8$(Sal)$_4$(SalH)$_2$(Py)$_4$] (salH=salicylic acid) and
[Mn$_{12}$O$_{12}$(OBz)$_{16}$(H$_2$O)$_4$].

It is preferable that the paramagnetic metal clusters according to the present invention have a relatively small charge overall. Most preferably, the paramagnetic metal clusters according to the present invention are neutral, although cationic and anionic clusters are included within the scope of the present invention. One advantage of neutral clusters is their potential for low osmolality. It is most preferable to provide MRI agents according to the present invention, having an osmolality equal to that of blood. An MRI agent having such an osmolality provides the maximum in patient safety and comfort.

Another important characteristic of the clusters according to the present invention, especially as those given in the Examples above, is their relatively high relaxivity ($\sim$6 nM$^{-1}$sec$^{-1}$ per Mn atom) compared to compounds containing only a single Mn atom (relaxivity $\sim$1 to 2 nM$^{-1}$sec$^{-1}$).

The foregoing has been a description of certain preferred embodiments of the present invention, but is not intended to limit the invention in any way. Rather, many modifications, variations and changes in details may be made within the scope of the present invention.

What is claimed is:

1. A contrast agent for magnetic resonance imaging comprising:
   a diagnostically effective amount of a paramagnetic metal cluster selected from the group consisting of
   [Mn$_3$(OAc)$_6$(bipy)$_2$]
   [Mn$_3$(OBz)$_6$(phen)$_2$]
   [Mn$_3$(OBz)$_6$(bipy)$_2$]
   [Mn$_3$(biphen)$_3$(OBz)$_2$(bipy)$_2$]
   [Mn$_3$(DBCat)$_4$(Py)$_4$] (DBCat=3,5-di-t-butylcatechol); and
   pharmaceutically acceptable carrier solution.

2. A contrast agent according to claim 1, wherein said paramagnetic metal cluster has a neutral charge.

3. A contrast agent according to claim 1, wherein said paramagnetic metal cluster has a anionic overall charge.

4. A contrast agent according to claim 1, wherein said paramagnetic metal cluster has a cationic overall charge.

5. A contrast agent for magnetic resonance imaging selected from the group consisting of
   [Mn(II)$_3$(OAc)$_6$(Phen)$_2$],
   [Mn(II)$_3$(OAc)$_6$(bipy)$_2$],
   [Mn(II)$_3$(O$_2$CPh)$_6$(bipy)$_2$], and
   [Mn(II)$_3$(O$_2$CPh)$_6$(phen)$_2$].

6. A contrast agent for magnetic resonance imaging comprising:
   a diagnostically effective amount of a paramagnetic metal cluster selected from the group consisting of
   [Mn$_4$O$_2$(OAc)$_6$(bipy)$_2$]

$[Mn_4O_2(OBz)_7(bipy)_2]$ $[Mn_4O_2(O_2CR)_7(PicH)_2]$— (R=Me, Et, Ph; PicH=picolinic acid)

$[Mn_4O_3Cl_4(O_2CR)_3(Py)_3]$ (R=Me, Ph)

$[M_4(DBCat)_4(Py)_6]$ (M=Mn, Fe)

$[Mn_4O_2(OAc)_6(Py)_2(dbm)_2]$ (dbm=dibenzoylmethane); and a pharmaceutically acceptable carrier solution.

7. A contrast agent for magnetic resonance imaging comprising:

a diagnostically effective amount of a paramagnetic metal cluster selected from the group consisting of $[Mn_6O_2(OBz)_{10}(Py)_2(MeCN)_2]$ $[Mn_6O_2(OBz)_{10}(Py)_4].Et_2O$ $[Mn_9O_4(OBz)_8(Sal)_4(SalH)_2(Py)_4]$ (salH=salicylic acid); and a pharmaceutically acceptable carrier solution.

* * * * *